United States Patent [19]

Luther

[11] 4,401,433
[45] Aug. 30, 1983

[54] APPARATUS FOR ADVANCING OVERSIZED CATHETER THROUGH CANNULA, AND THE LIKE

[76] Inventor: Ronald B. Luther, 530 King Rd., Newport Beach, Calif. 92663

[21] Appl. No.: 159,123

[22] Filed: Jun. 13, 1980

[51] Int. Cl.³ .............................................. A61M 5/00
[52] U.S. Cl. .................................. 604/159; 604/281
[58] Field of Search .................. 128/200.26, 348, 349, 128/214.4; 72/410; 29/243.56; 226/119, 189; 138/101, 161, 174

[56] References Cited

U.S. PATENT DOCUMENTS 3,774,605  11/1973  Jewett .............................. 128/214.4

FOREIGN PATENT DOCUMENTS 1810804  6/1970  Fed. Rep. of Germany ... 128/214.4
440731  5/1912  France ........................... 128/349 R
1295501  5/1962  France .................................. 72/410

Primary Examiner—Kyle L. Howell
Assistant Examiner—Max F. Hindenburg
Attorney, Agent, or Firm—Willie Krawitz

[57] ABSTRACT

A catheter is provided having a larger size than the cannula through which it is introduced into a puncture site, such as a vein.

The oversized catheter is preferably elliptical shaped, and, prior to introduction into the cannula, the catheter is folded to reduce its overall cross sectional area. The catheter is then advanced through the smaller cannula either manually, or by advancing roller drives, and then inserted into the patient.

Use of an oversized catheter reduces the possibility of it slipping out from a vein, and its elliptical configuration is useful in conforming to a vein shape for improved retention therein and laminar blood flow.

7 Claims, 6 Drawing Figures

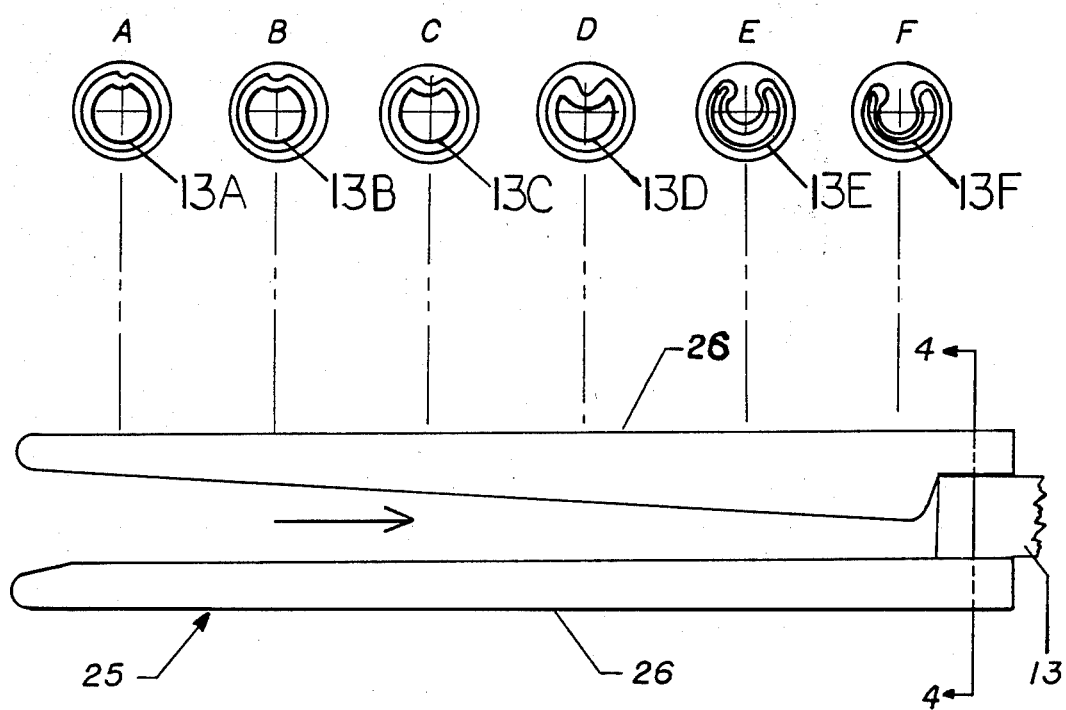
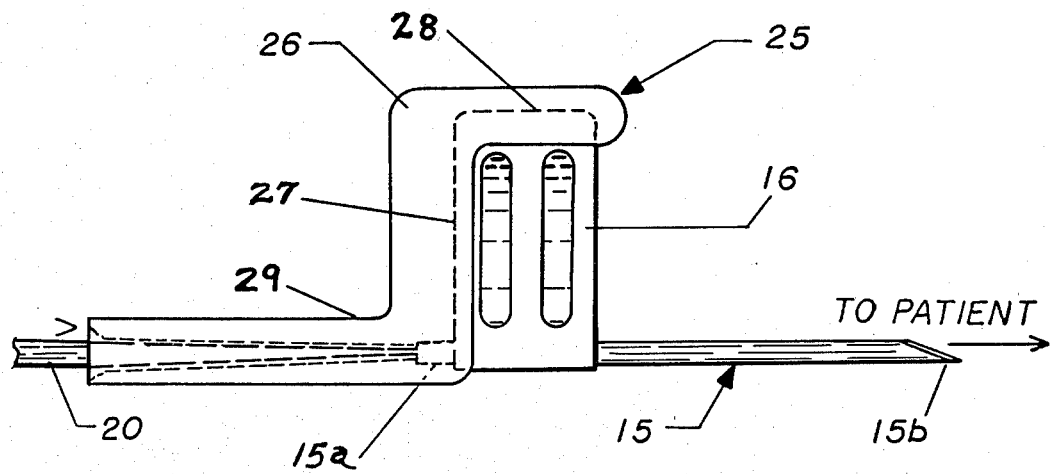

APPARATUS FOR ADVANCING OVERSIZED CATHETER THROUGH CANNULA, AND THE LIKE

BACKGROUND OF THE INVENTION

This invention relates to a new and improved catheter, and more specifically to a catheter which occupies a larger cross sectional area than the cannula through which it fits. This enables the catheter to be inserted through a cannula having a smaller cross section than the catheter itself and into a vein orifice of smaller size than the catheter.

The problem which occurs when using a conventional catheter and cannula arrangement is the possibility that because the cannula has a larger diameter than the catheter, it will obviously create a larger perforation in the vein than the catheter; consequently, the catheter may slip out of the oversized perforation. Another problem associated with catheters is the fact that veins tend to be elliptical in cross section, however, catheters are manufactured with a circular configuration. Hence, even if a somewhat undersized catheter does not present a problem, where a catheter and vein have mismatched shapes, a potentially loose fit is possible. A loose fit may result in intravenous leakage or in the catheter simply slipping out from a vein, even when seemingly adequately secured.

THE INVENTION

According to the invention, there is provided an assembly of a cannula, needle or the like and a folded catheter, the cross sectional area of the catheter being greater than the interior cross sectional area of the cannula. Following penetration of a vein by the cannula, the catheter is inserted into the vein in a folded condition. The resiliency of the catheter material, which is usually a rubber, elastomer, or similar material enables the fold to expand, and the catheter then assumes its normal shape in the vein. After the catheter has been inserted into the vein, the cannula is retracted from the vein, removed from the patient, and then separated from the catheter. Since the puncture in the vein is smaller than the catheter diameter, the possibility of the catheter slipping from a vein is greatly reduced.

Preferably, the catheter is elliptically shaped, and this enables it to be easily folded. An elliptically shaped catheter has the added advantage of tending to conform with the shape of a vein which tends to have an elliptical configuration. This, in turn, results in an improved catheter-vein fit and reduces the possibility of the catheter slipping out from a vein. However, for certain uses, the catheter may be utilized in a round configuration.

The catheter may be folded into the cannula and advanced manually, or may be folded and advanced through the cannula by mechanical means, such as roller drives.

BRIEF DESCRIPTION OF THE DRAWINGS

FIGS. 2(A) and 2(B) are cross sectional views in end elevation of an elliptical shaped catheter in an unfolded condition, and when folded for insertion into a cannula, needle or the like;

FIG. 3 is a cross sectional view in side elevation showing another embodiment of a device for producing a folded catheter;

FIG. 5 is a side elevation view in axial section, showing the catheter folding device of FIG. 1 operatively connected to a cannula and adapted for manual insertion of the catheter therethrough; and, FIGS. 6 A-F illustrate cross-sectional views of the arm showing the internal arm configurations and conforming catheter shapes.

DESCRIPTION OF THE PREFERRED EMBODIMENTS

Figure 1:
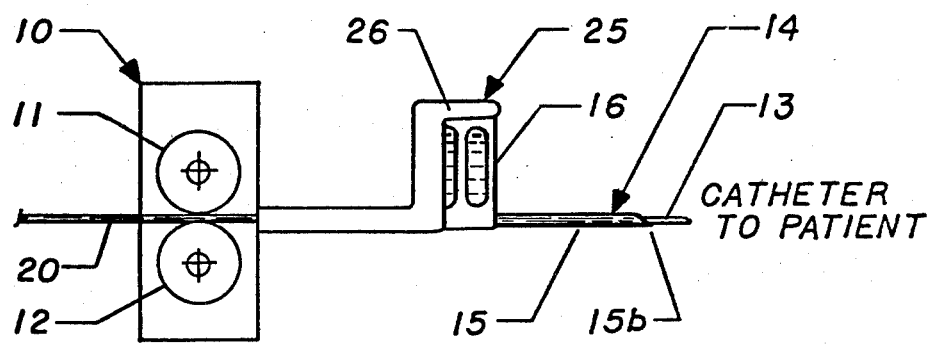
FIG. 1 is a side elevation view showing one embodiment of a device attached to a cannula for producing a folded catheter, and a roller drive for advancing the catheter through the cannula.

A portion of the catheter advance apparatus 10 of this invention is shown in FIG. 1, and includes roller drives 11, 12 positioned on either side of a catheter 20 which it drives through a cannula 14. A suitable cannula is disclosed in my U.S. Pat. No. 4,100,393 and provides a cannula body 15 having a distal end 15a, leading edge 15b, and holder wings, one wing 16 being shown welded to the cannula body.

As illustrated in FIGS. 1 and 5, one embodiment of the catheter folding device 25 provides compression arms, one arm 26 being shown. The compression arm 26 is slotted 27, 28 to engage the edges of the wing 16. The compression head 29 for folding the catheter is of a resilient sheet structure similar to that shown in FIG. 4., and is integral with the arms and extends rearwardly thereof.

After leaving the cannula 14, the folded catheter tube 13 is advanced by the roller drives 11 and 12 through the cannula after the latter has been inserted into the vein of a patient. Following insertion of the catheter into the patient's vein, the catheter advance apparatus 10 and catheter folding device 25 are disengaged from the cannula 14; the cannula is then withdrawn from the patient and the holder wings are folded together. This causes the cannula to split longitudinally and be disengaged from the catheter.

When employed manually, i.e., without use of advance rollers, as in FIG. 5, the cannula element 15 is simply inserted through the compression head 29 of the catheter folding device 25. The catheter is manually folded by the head and advanced manually through the cannula toward the leading edge 15b.

Figure 2A:
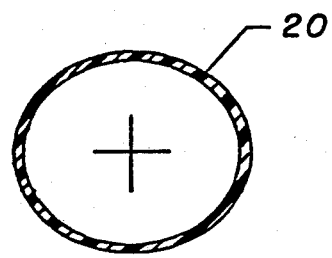
Figure 2B:
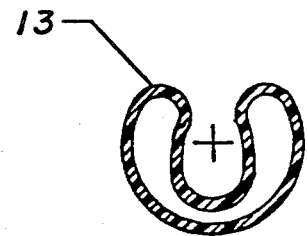

Preferably, the catheter in the unfolded configuration 20 is shaped elliptically as shown in FIG. 2A, and this facilitates folding of the catheter 13 as in FIG. 2B so that in the cannula, it will occupy a smaller cross sectional area than in the unfolded condition. Also, the elliptical shape usually matches the vein shape, and this enables a better fit. When properly sized, the catheter in its folded condition will occupy a smaller cross sectional area than the cannula so that upon insertion into a puncture site, such as a patient's vein, the catheter will occupy a larger cross sectional area than the cannula. Hence, there will be less tendency for the catheter to slip out or be dislodged from the vein. While an elliptical shape is preferred, other configurations are also suitable, such as a round form shown in FIGS. 6 A-F.

Typical materials which may be employed as the catheter include polyurethanes, rubbers and elastomers; these materials are flexible and may be sterilized. Also, they have sufficient plastic memory to enable the catheter to unfold into the elliptical or round shape from their respective folded condition after being inserted through the cannula.

Figure 4:
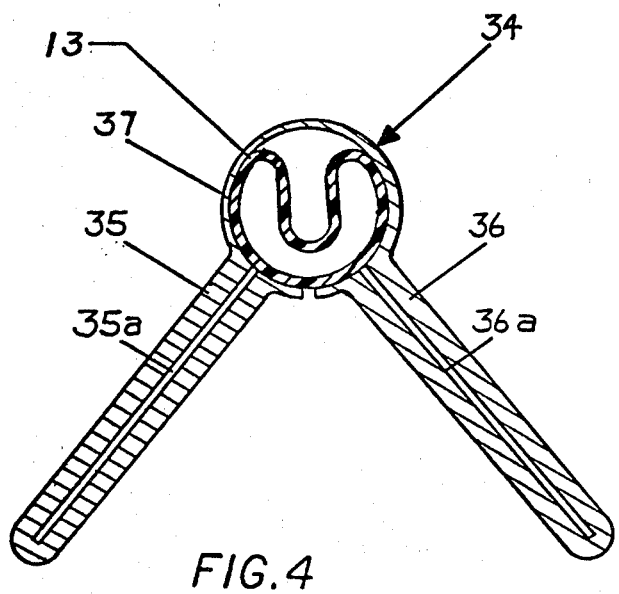
FIG. 4 is a cross sectional view of the device taken along lines 4—4 of FIG. 3.

Another embodiment of a catheter folding device 34 for folding the catheter is shown in FIGS. 3 and 4, and includes compression arms 35, 36 having respective slots 35a, 36a through which the cannula wings fit. The compression arms are attached to a hollow compression head 37 for compressing the catheter 20 into a fold. The compression head may be constructed of a resilient sheet metal material to outwardly bias the arms 35, 36 and provide better handling properties. The extent of catheter folding in the device of FIG. 4 corresponds to that shown in FIG. 6 (F).

The interior of the arms 35, 36 are configured to shape the unfolded catheter 20 into a folded shape commencing from an initial fold 13A to the final folded shape 13F of FIG. 6F.

The apparatus of this invention enables a folded catheter to be formed for insertion into a cannula, needle, or the like in order to produce a close fit with a vein for better retention therein, minimal patient discomfort and improved laminar blood flow.

I claim:

1. An apparatus for introducing a catheter into a vein perforation, and the like through the barrel of a cannula, needle and the like, the cannula providing holder wings for separating the barrel, comprising:
   a. catheter means;
   b. a cannula with holder wings;
   c. compression means for folding the catheter from its normal configuration having a larger cross sectional area than the cannula bore into a cross sectional area smaller than its normal configuration, the compression means including:
      i. a resilient, hollow compression head having an open and closed position, and adapted in the open position to receive an unfolded catheter lengthwise, and in the closed position to compress the catheter from the unfolded to a folded configuration along the catheter length;
      ii. normally outwardly biased, opposed compression arms mounted at either side of the compression head, and adapted to be forced together thereby closing the head and folding the catheter lengthwise, each arm having a longitudinal slot, each holder wing of the cannula being inserted into and engagement with the slot;
   d. advancing means to forward the folded catheter through the cannula into a vein perforation produced by the cannula while engaged by the wings and compression means, the catheter being constructed of a flexible material having a sufficient plastic memory, whereby it will unfold from its smaller cross sectional area into its larger cross sectional area, thereby tightly fitting into the vein and perforation, the cannula being adapted for:
      i. removal by retraction from the vein;
      ii. disengagement of the wings from the longitudinal slots of the compression arms; and,
      iii. removal from the catheter, by flexing the wings to break apart the cannula.

2. The apparatus of claim 1, in which the unfolded catheter has a round cross section.

3. The apparatus of claim 1, in which the unfolded catheter has an elliptical cross section.

4. The apparatus of claim 1, comprising rotating roller drives to advance the folded catheter through the cannula bore.

5. The apparatus of claim 1, in which the catheter is selected from the class of materials consisting of: polyurethanes, rubbers, and elastomers.

6. The apparatus of claim 1, in which the catheter is advanced manually.

7. The apparatus of claim 1, in which the compression head is constructed of a resilient sheet material.

* * * * *